United States Patent
Chan et al.

(10) Patent No.: US 8,299,913 B2
(45) Date of Patent: Oct. 30, 2012

(54) BLOOD PRESSURE MEASUREMENT AND REMINDER SYSTEM

(75) Inventors: Raymond Chan, Hong Kong (CN); Mun Hoong Leong, Hong Kong (CN); Li Li, Hong Kong (CN)

(73) Assignee: IDT Technology Limited, Hunghom, Kowloon (HK)

(*) Notice: Subject to any disclaimer, the term of this patent is extended or adjusted under 35 U.S.C. 154(b) by 628 days.

(21) Appl. No.: 12/534,862

(22) Filed: Aug. 4, 2009

(65) Prior Publication Data
US 2010/0194572 A1    Aug. 5, 2010

Related U.S. Application Data

(60) Provisional application No. 61/086,148, filed on Aug. 4, 2008.

(51) Int. Cl.
*G08B 1/08* (2006.01)
(52) U.S. Cl. ........... 340/539.12; 340/309.7; 340/286.07; 600/300
(58) Field of Classification Search ............. 340/286.07, 340/539.12, 573.1, 309.7, 309.15, 309.16; 600/300, 490; 705/3
See application file for complete search history.

(56) References Cited

U.S. PATENT DOCUMENTS

| | | | | |
|---|---|---|---|---|
| 5,988,836 A * | 11/1999 | Swarens | ........................ | 362/364 |
| 7,312,709 B2 * | 12/2007 | Kingston | .................... | 340/573.1 |
| 7,956,727 B2 * | 6/2011 | Loncar | ..................... | 340/309.16 |
| 2002/0077557 A1 * | 6/2002 | Cheng | ........................... | 600/490 |
| 2003/0020599 A1 * | 1/2003 | Somers et al. | ............ | 340/309.15 |
| 2005/0031102 A1 * | 2/2005 | Kraus et al. | ................ | 379/114.2 |
| 2008/0201168 A1 * | 8/2008 | Brown | .............................. | 705/2 |
| 2008/0246617 A1 * | 10/2008 | Tao et al. | ................... | 340/573.1 |

FOREIGN PATENT DOCUMENTS

| | | |
|---|---|---|
| EP | 1714611 A | 10/2006 |
| WO | 03088890 A | 10/2003 |
| WO | 2006133735 A1 | 12/2006 |

* cited by examiner

*Primary Examiner* — Brent Swarthout
(74) *Attorney, Agent, or Firm* — Eagle IP Limited; Jacqueline C. Lui

(57) ABSTRACT

A blood pressure measurement and reminder system comprising a blood pressure measuring unit, a reminder unit, and an input unit is disclosed. The system is configured to transmit reminder signal(s) noticeable to its users for alerting them to take blood pressure measurement within a pre-determined measurement time schedule, and send confirmation signal(s) to the reminder unit to switch off the reminder state once the user has successfully taken a blood pressure measurement.

9 Claims, 3 Drawing Sheets

BLOOD PRESSURE MEASUREMENT AND REMINDER SYSTEM

CROSS-REFERENCE TO RELATED APPLICATION

This application claims benefit under 35 U.S.C. §119(e) of U.S. Provisional Application having Ser. No. 61/086,148 filed Aug. 4, 2008, which is hereby incorporated by reference herein in its entirety.

FIELD OF INVENTION

The present invention relates to a blood pressure measurement system. In particular, this invention relates to a blood pressure measurement system with a reminder feature.

BACKGROUND OF INVENTION

In recent years, self-monitoring of blood pressure by patients at home has earned increasing interests among hypertension societies worldwide. Medical professionals believe that the home blood pressure monitoring practice would improve in patients' compliance and hypertension control rates, and assist in early detection of hidden diseases such as white coat hypertension and masked hypertension phenomena.

SUMMARY OF INVENTION

In the light of the foregoing background, it is an object of the present invention to provide an improved blood pressure measurement system.

Accordingly, the present invention, in one aspect, is a blood pressure measurement and reminder system which comprises a blood pressure measuring unit, a signal transmitter, and at least one reminder unit. The blood pressure measuring unit further comprises a measurement subunit adapted to allow the user to take blood pressure measurements therewith. The signal transmitter connects to the measuring subunit and is capable of transmitting signal(s). The reminder unit, adapted to be switchable between a reminder state and a reminder-off state, comprises an alarm subunit adapted to send reminder signal(s) to the user to remind the user to take blood pressure measurement, and a communication subunit adapted to receive signal(s) transmitted from the signal transmitter. Further, the reminder unit is remote and physically separate from the blood pressure measuring unit and capable of wireless interaction and wireless communication. The reminder unit is triggerable to switch to the reminder state according to the user's input. Whenever the user has made a blood pressure measurement within a measurement time schedule, the signal transmitter will transmit a confirmation signal(s) to the communication subunit to switch the reminder unit from the reminder state to the reminder-off state.

In one non-limiting embodiment, if the blood pressure measurement has not been taken by the user beyond the measurement time schedule, the communication subunit would send external communication signal(s) ("secondary reminder(s)") to a device external to the system.

In another aspect of the instant invention, a reminder method for taking blood pressure measurement, with the use of the blood pressure measurement reminder system as described in this invention, is provided in which the system first receives a measurement time schedule from the user. Then, it checks whether a starting time of the measurement time schedule has been reached. Once the starting time is reached, the reminder unit would be triggered to switch to the reminder state and the alarm subunit is triggered to send the reminder signal(s) to the user. Upon taking the blood pressure measurement by the user, the signal transmitter would transmit the confirmation signal(s) to the communication subunit. Thereafter, the reminder unit would be triggered to switch from the reminder state to the reminder-off state.

The implementation of the blood pressure measurement and reminder system according to the instant invention may provide an efficient and reliable way to remind and prompt its users on when they should take the blood pressure measurements by providing the reminder unit that can be installed anywhere in the house, especially in places where the users will frequently stay (e.g. living room, kitchen, or washroom). In addition, the reminder unit will be automatically switched off by a signal from the signal transmitter when the blood pressure measurement has been taken, rather than allowing the user to switch it off manually. This is particularly beneficial to patients suffering early dementia and/or short-term memory problems who may forget what they want to do the moment they switch the reminder unit to the reminder-off state and forget to take their blood pressure measurement even as they walk towards the blood pressure measuring device despite the good intentions. Using the device according to the present invention, there is no longer the possibility that the user would fail to take their blood pressure measurement if they have the above-mentioned reminder switched on.

DETAILED DESCRIPTION OF THE PREFERRED EMBODIMENTS

As used herein and in the claims, "comprising" means including the following elements but not excluding others.

Figure 1:
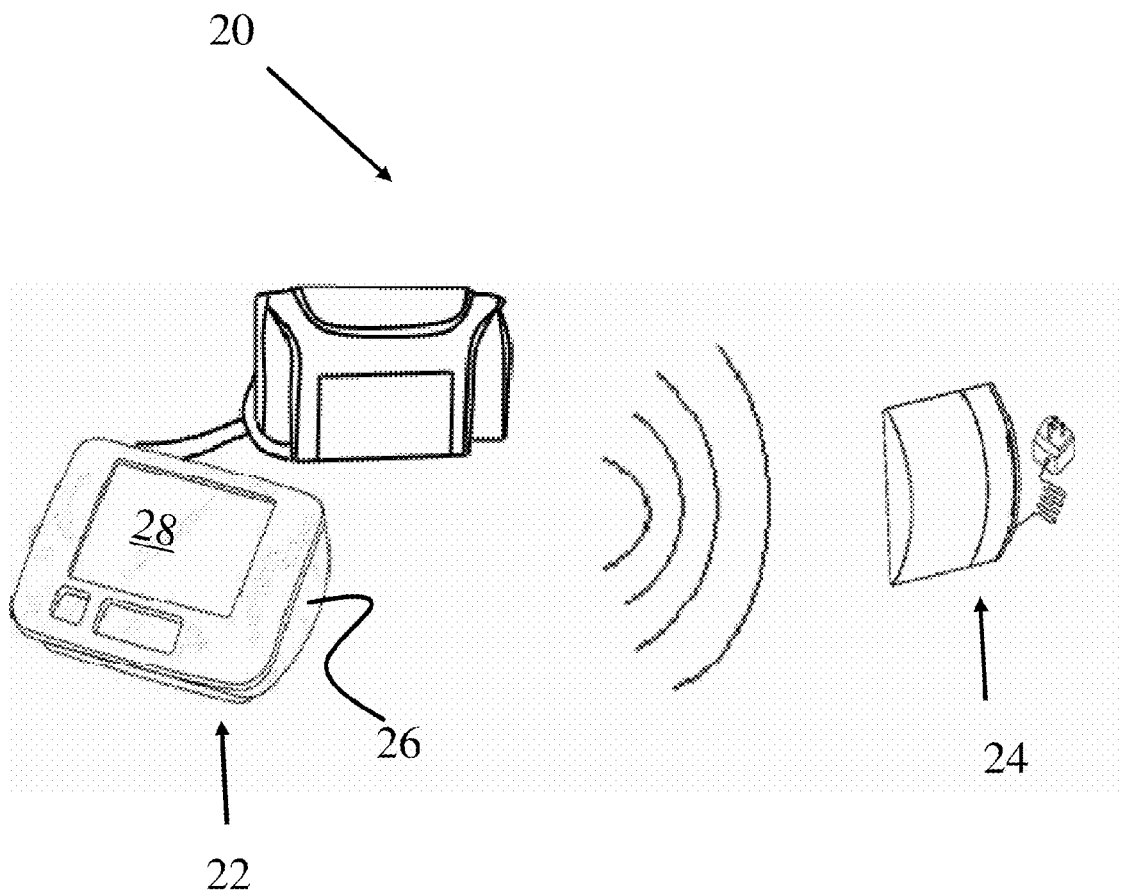
FIG. 1 is a perspective view of the blood pressure measurement and reminder system according to one embodiment of the present invention.

Referring first to FIG. 1, in one embodiment of the present invention is a blood pressure measurement and reminder system 20 which comprises a blood pressure measuring unit 22 and a reminder unit 24. The blood pressure measuring unit 22 in the example shown includes a case 26 within which a cuff, a pressure sensor, a signal transmitter, a microprocessor, and an input subunit are provided and these subunits are interconnected inside the case 26. Also, the blood pressure measuring unit 22 as shown in this example has a display 28 disposed on the case 26.

Figure 2:
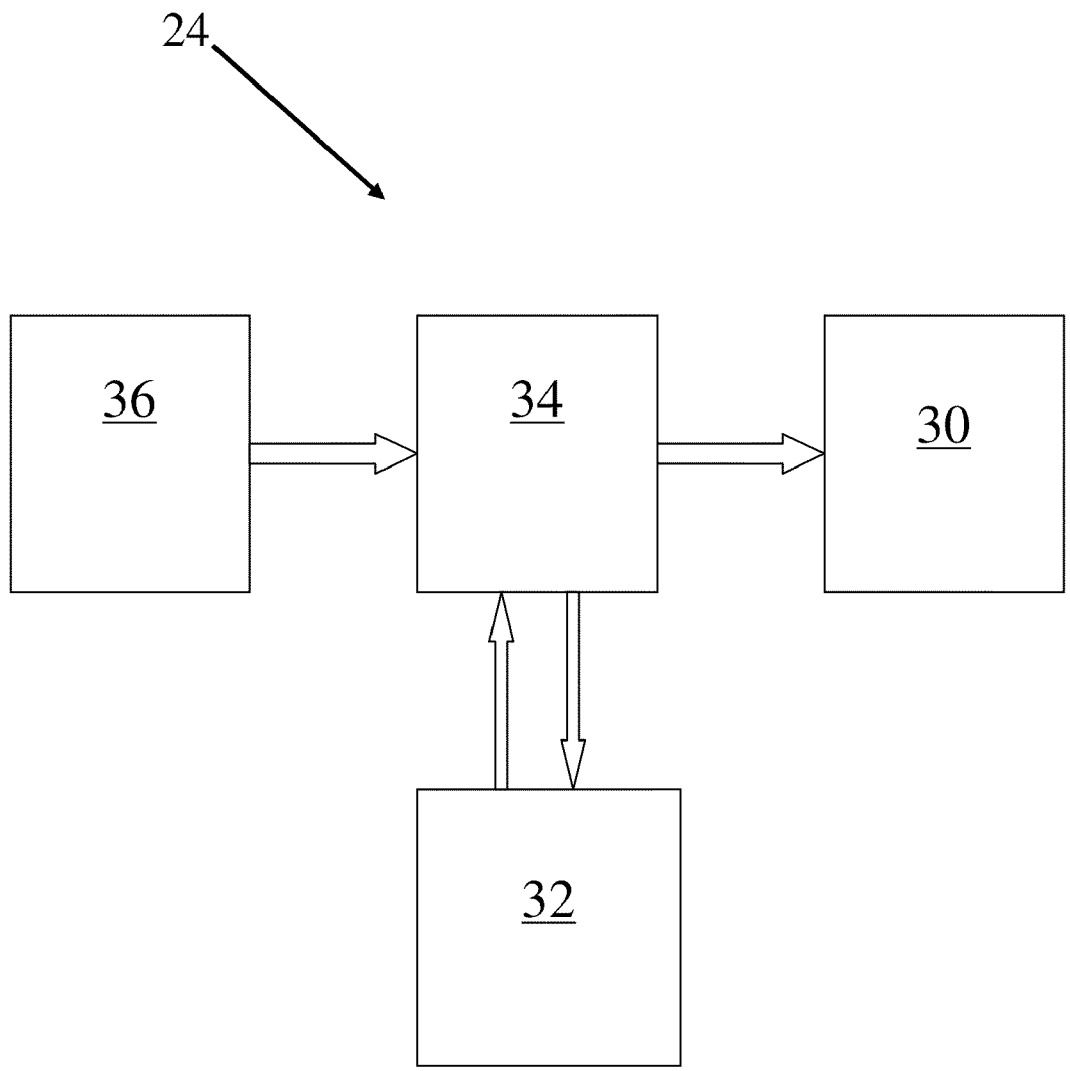
FIG. 2 is a block diagram of the reminder unit to demonstrate the interaction between different subunits therewithin according to the same embodiment of the present invention.

As shown in FIG. 2, the reminder unit 24 comprises an alarm subunit 30, a communication subunit 32, and a controller subunit 34, in which the controller subunit 34 is adapted to connect to the other two subunits. In one embodiment, the reminder unit 24 further comprises a setting subunit 36 connected to the controller subunit 34. As illustrated in the example shown in FIG. 1, the reminder unit 24 has a curved front surface for enhancing the display of light emitted therefrom, and a flat back surface for fixing the reminder unit 24 onto the wall.

Figure 3:
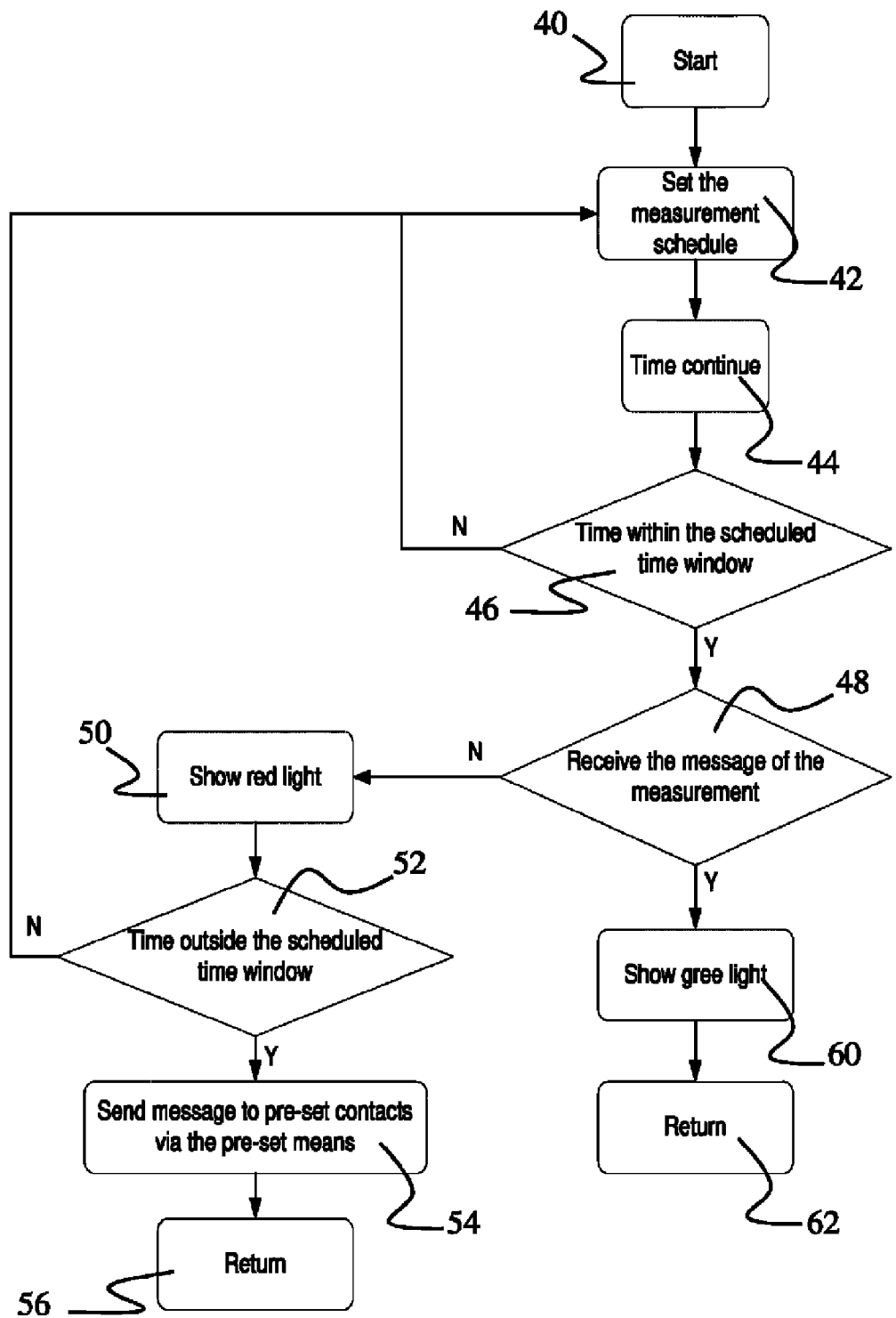
FIG. 3 is a flow chart for the operation mechanics of the blood pressure measurement and reminder system according to the same embodiment of the present invention.

FIG. 3 shows the mechanics of the operation of the blood pressure measurement and reminder system described above.

Before the operation, the user first sets up a measurement time schedule via the input subunit provided within the system 20 (Box 42). In one embodiment, the setting unit 36 of the reminder unit 24 (as shown in FIG. 2) can also be used as an alternative means for inputting the measurement time schedule. In another embodiment, the input parameters include the starting and ending times of the measurement time schedule, the frequency of the emission of the reminder signal, the type of reminder signal emitted, etc. The time schedule can also be based on clinically tested protocols or protocols recommended by medical professionals. In one embodiment, the measurement time schedule is transmitted to all other units within the system 20 upon entering by the user.

During the operation, the reminder unit 24 is triggered to switch to the reminder state once the time enters each measurement time schedule, in which the alarm subunit 30 will emit a reminder signal for alerting the user to take blood pressure measurement. In one embodiment, the reminder signal is a visual or audio signal, or a combination thereof, which is noticeable to the user. In the example shown, a red light will be shown on the reminder unit 24 (Box 50) to remind the user that blood pressure measurement has yet been taken. If the user forgets to take the blood pressure measurement within the measurement time schedule, no confirmation signal will be transmitted from the signal transmitter to the communication subunit 32 of the reminder unit 24 and the reminder unit 24 remains in the reminder state.

When the user has taken his/her blood pressure measurement at the blood pressure measuring unit 22 within the measurement time schedule, a confirmation signal will then be transmitted from the signal transmitter to the communication subunit 32 of the reminder unit 24. Then, the reminder unit 24 will be triggered to switch from the reminder state to the reminder-off state. In the example shown, at the reminder-off state, the reminder unit 24 will display a green light as a completion signal to indicate that blood pressure measurement has been taken within the time schedule window (Box 60).

In another embodiment, if no blood pressure measurement has been taken beyond the time schedule window, the communication subunit 32 will be triggered to transmit an external communication signal(s) ("secondary reminder(s)") to a device external to the system. In one embodiment, the secondary reminders are transmitted to an external device of the user, such as an SMS message on the telephone of the user.

When making a blood pressure measurement at the blood pressure measuring unit 22, the user first wraps the cuff around his/her arm. Upon activating the blood pressure measuring unit 22, pressure oscillations from the cuff will be sensed by the pressure sensor, and the oscillation data will be forwarded to the microprocessor. Consequently, the microprocessor will calculate the corresponding blood pressure based on the pre-installed algorithms. The results will then be shown on the display 28.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, the concept of the blood pressure measurement and reminder system according to the instant invention can be extended to other applications that require regular reminders, such as the intake of medicines. In this embodiment, the blood pressure measurement unit will be replaced by a medicine box that has, for example, individual holding unit for each dose of medication. When the time is reached for the medication to be taken, the medicine box will send a signal to the reminder unit. Once the user has removed the medicine from the appropriate holding unit, the medicine box can send another signal to the reminder unit to switch off the reminder unit. It is also not necessary to have only one reminder unit in each system; any numbers of reminder units can be implemented.

In addition, a centralized reminder system can be tailor-made and designed to monitor several applications at the same time according to the user's preferences. For instance, the concepts of blood pressure measurement and medicine intake can be combined and simultaneously monitored by one reminder system. In this embodiment, the centralized reminder system connects concurrently with the blood pressure measuring unit and the medicine box unit. When the reminder unit is triggered to the reminder state, it needs to receive confirmation signals from both the blood measuring unit and the medicine box unit before it can be switched back to the reminder-off state. Thus, the user has to make both the blood pressure measurement and medicine retrieval from the medicine box before the reminder unit can be switched off.

Further, the system can be designed to send remote reminders to its users when the users are away from home.

Although a display disposed on the blood pressure measuring unit is used for showing the results of the blood pressure measurement, it is clear that a projector module can also be implemented to the system for projecting the results on a wall for better illustration thereof.

In one variation, the blood pressure measuring unit may also comprise a voice processor which can vocally inform the user the measurement result. In a further variation, the blood pressure classification for the measurement result can also be informed to the user once such classification data has been pre-loaded in the microprocessor.

In one embodiment, the input unit can be a keyboard or an input interface such as a wireless or universal serial bus (USB) connection interface for the user to input his/her measurement time schedule.

In another variation, secondary reminders can be transmitted to a pre-determined destination such as a local healthcare institution or family members of the user. In one embodiment, contact details of the pre-determined destination are entered into the reminder unit through the setting subunit 36. The secondary reminder can also be sent from the signal transmitter instead of the communication subunit 32.

What is claimed is:

1. A reminder method for taking blood pressure measurement in a blood pressure measurement reminder system, wherein said blood pressure measurement reminder system comprises:
   I. a blood pressure measuring unit comprising a measurement subunit adapted for a user to take blood pressure measurement;
   II. a signal transmitter connected to said measuring subunit and adapted for transmitting signal(s);
   III. at least one reminder unit comprising:
      i. an alarm subunit adapted to send reminder signal(s) to remind said user to take said blood pressure measurement; and
      ii. a communication subunit adapted to receive signal(s) transmitted from said signal transmitter;
   wherein said reminder unit is adapted to be switchable between a reminder state and a reminder-off state;
   IV. a projector module for projecting a result of said blood pressure measurement and a blood pressure classification thereof;

wherein said reminder unit is remote and physically separate from said blood pressure measuring unit and capable of wireless interaction and wireless communication therewith; said reminder unit is triggerable to switch to said reminder state according to said user's input; wherein upon taking said blood pressure measurement by said user within a measurement time schedule, said signal transmitter transmits confirmation signal(s) to said communication subunit to switch said reminder unit from said reminder state to said reminder-off state; said reminder method comprising the steps of:
- a). receiving said measurement time schedule from said user;
- b). checking whether a starting time of said measurement time schedule has been reached;
- c). triggering said reminder unit to switch to said reminder state and triggering said alarm subunit to send said reminder signal(s) to said user once said starting time is reached;
- d). transmitting said confirmation signal(s) from said signal transmitter to said communication subunit of said reminder unit upon taking said blood pressure measurement by said user;
- e). triggering said reminder unit to switch from said reminder state to said reminder-off state; and
- f). projecting said result of said blood pressure measurement and said blood pressure classification thereof on a wall.

2. The method according to claim 1 wherein said step (c) further comprises transmitting external communication signal(s) as secondary reminder(s) to a device external to said system when said blood pressure measurement has not been taken by said user beyond said measurement time schedule.

3. The method according to claim 1 wherein said blood pressure measuring unit further comprises:
- a). a cuff;
- b). a pressure sensor;
- c). a microprocessor; and
- d). an input subunit adapted for said user to input said measurement time schedule.

4. The method according to claim 3 wherein said blood pressure measuring unit further comprises a display adapted to show said result of said blood pressure measurement.

5. The method according to claim 3 wherein said blood pressure measuring unit further comprises a voice processor adapted to vocally inform said user said result.

6. The method according to claim 1 wherein said reminder unit further comprises a controller subunit adapted to connect said alarm subunit and said communication subunit.

7. The method according to claim 6 wherein said reminder unit further comprises a setting subunit adapted for said user to input said measurement time schedule.

8. The method according to claim 1 wherein said reminder signal sent from said alarm subunit is a visual signal, an audio signal, or a combination thereof, noticeable to said user.

9. The method according to claim 1 wherein said system further comprises a keyboard, a wireless, or a universal serial bus connection interface adapted for said user to input said measurement time schedule.

* * * * *